United States Patent [19]

Fernandez Fernandez et al.

[11] Patent Number: 5,041,461
[45] Date of Patent: Aug. 20, 1991

[54] ORGANIC COMPOUNDS AND THEIR USE AS PHARMACEUTICALS

[75] Inventors: Maria I. Fernandez Fernandez, Madrid, Spain; Terrence M. Hotten, Farnborough; David E. Tupper, Reading, both of England

[73] Assignee: Lilly Industries Limited, Basingstoke, England

[*] Notice: The portion of the term of this patent subsequent to Feb. 22, 2007, has been disclaimed.

[21] Appl. No.: 412,686

[22] Filed: Sep. 26, 1989

[30] Foreign Application Priority Data

Sep. 30, 1988 [GB] United Kingdom ............... 8823042

[51] Int. Cl.$^5$ ............... A61K 31/38; C07D 333/32
[52] U.S. Cl. ............... 514/422; 514/299; 514/326; 514/444; 546/112; 546/212; 548/527; 549/62; 549/64
[58] Field of Search ............... 548/827; 514/422, 444, 514/299, 326; 549/62, 64; 546/112, 212

[56] References Cited

U.S. PATENT DOCUMENTS

| 3,177,252 | 4/1965 | Thominet | 260/559 |
| 3,342,826 | 9/1967 | Miller et al. | 260/294 |
| 3,932,503 | 1/1976 | Weber et al. | 260/553 DA |
| 4,123,550 | 10/1978 | Untch et al. | 424/275 |
| 4,221,815 | 9/1980 | Weyer et al. | 424/319 |
| 4,321,378 | 3/1982 | Dostert et al. | 544/321 |
| 4,560,751 | 12/1985 | Seybold | 544/60 |
| 4,904,686 | 2/1990 | Fernandy et al. | 514/422 |

FOREIGN PATENT DOCUMENTS

| AU14705 | 10/1988 | Australia . |
| 60235 | 9/1982 | European Pat. Off. . |
| 65295 | 11/1982 | European Pat. Off. . |
| 170024 | 2/1986 | European Pat. Off. . |
| 171739 | 2/1986 | European Pat. Off. . |
| 297697 | 1/1989 | European Pat. Off. . |
| 1937759 | 9/1970 | Fed. Rep. of Germany . |
| 2952279 | 6/1981 | Fed. Rep. of Germany . |
| 63-261778 | 11/1988 | Japan . |

OTHER PUBLICATIONS

Consiglio, et al., *J. Chem. Soc. Perkin Trans. II*, 1983, 1559–1561.
C. A. 72, 3226a (1970).
C. A. 67, 2167w (1967).
C. A. 101, 122562j (1984).
C. A. 100, 84964m (1984).
*Anales de la Real Academia de Pharmacia*, 42, (4), 563 (1976), (Chemical Abstracts 87: 23197e)
*Anales de Quimica*, 70 (12), 974 (1974) (Chemical Abstracts 83: 178980w).

Primary Examiner—C. Warren Ivy
Assistant Examiner—Celia Chang
Attorney, Agent, or Firm—Robert A. Conrad; Leroy Whitaker

[57] ABSTRACT

A pharmaceutically-active compound of the formula

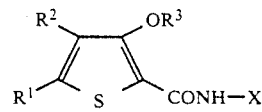

in which $R^1$ is $C_{1-4}$ alkythio, $C_{1-4}$ alkylsulphinyl or $C_{1-4}$ alkylsulphonyl, $R^2$ is $C_{1-4}$ alkyl, $R^3$ is $C_{1-4}$ alkyl or $C_{2-4}$ alkenyl, and X is (i) —$(CH_2)_nN(R^4)_2$ where each $R^4$ independently is $C_{1-4}$ alkyl, $C_{2-4}$ alkenyl or optionally substituted $C_6H_5CH_2$—, and n is 1, 2 or 3, or (ii) a 5- to 8-membered alicyclic group containing one or two nitrogen atoms and directly attached to the amido nitrogen or attached by a $C_{1-3}$ alkylene chain; and salts thereof.

6 Claims, No Drawings

ORGANIC COMPOUNDS AND THEIR USE AS PHARMACEUTICALS

This invention relates to organic compounds, their preparation and use as pharmaceuticals.

The compounds of the invention are of the formula:

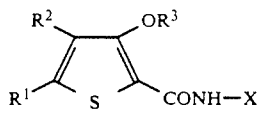

in which $R^1$ is $C_{1-4}$ alkylthio, $C_{1-4}$ alkylsulphinyl or $C_{1-4}$ alkylsulphonyl, $R^2$ is $C_{1-4}$ alkyl, $R^3$ is $C_{1-4}$ alkyl or $C_{2-4}$ alkenyl, and X is (i) $-(CH_2)_nN(R^4)_2$ where each $R^4$ independently is $C_{1-4}$ alkyl, $C_{2-4}$ alkenyl or optionally substituted $C_6H_5CH_2-$, and n is 1, 2 or 3, or (ii) a 5- to 8-membered alicyclic group containing one or two nitrogen atoms and directly attached to the amido nitrogen or attached by a $C_{1-3}$ alkylene chain; and salts thereof.

When X is an alicyclic group it is preferably attached at one of its carbon atoms and can contain an additional hetero atom as in a morpholino group or two nitrogen atoms as in piperazino, but preferably it contains only a single nitrogen atom. When the alicyclic group is attached via an alkylene chain, the chain is preferably of the form $-(CH_2)_n-$ where n is 1, 2 or 3 and X is thus of the formula $-(CH_2)_nY$ where Y is an alicyclic ring attached at one of its carbon atoms. The alicyclic ring can be substituted by, for example, a $C_{1-4}$ alkyl, $C_{2-4}$ alkenyl or optionally substituted $C_6H_5CH_2-$ group.

The following are preferred examples of alicyclic groups:

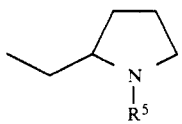

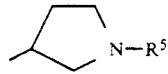

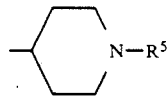

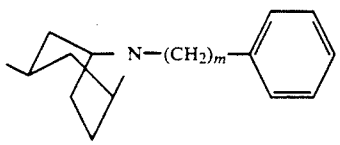

where m is 1, 2 or 3 and $R^5$ is $C_{1-4}$ alkyl, $C_{2-4}$ alkenyl or optionally substituted $C_6H_5CH_2-$.

The compounds of the invention and their pharmaceutically-acceptable salts have useful effects on the central nervous system.

When reference is made to $C_{1-4}$ alkyl this includes, for example, methyl, ethyl, n-propyl, isopropyl and butyl, and is especially methyl or ethyl. The groups $C_{1-4}$ alkylthio, $C_{1-4}$ alkylsulphinyl and $C_{1-4}$ alkylsulphonyl consist of these alkyl groups attached to the thiophene ring through a sulphur atom, a sulphinyl $(-SO-)$ and sulphonyl group $(-SO_2-)$, respectively.

When $R^3$, $R^4$ or $R^5$ is $C_{2-4}$ alkenyl, it is preferably vinyl or propenyl, and when $R^4$ and $R^5$ is optionally substituted $C_6H_5CH_2-$, although preferably unsubstituted, it can be substituted on the phenyl group with one or more, preferably one to three, substituents selected from, for example, halogen, $C_{1-4}$ alkyl, $C_{1-4}$ alkoxy, hydroxy, nitro, cyano, amino, carboxy and carboxamido.

A preferred group of compounds is one of formula (I) above, in which X takes the value defined in (ii), that is, X is a 5- to 8-membered alicyclic group, and X is preferably a group of the formula

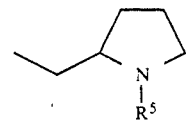

in which $R^5$ is $C_{1-4}$ alkyl, $C_{2-4}$ alkenyl or $C_6H_5CH_2-$, the most preferred example of X being that in which $R^5$ is ethyl.

With regard to $R^2$ and $R^3$, the preferred values are methyl, and $R^1$ is preferably methylsulphinyl or methylsulphonyl, and especially methylthio.

Preferred compounds of the invention include:

N-[(1-ethyl-2-pyrrolidinyl)methyl]-3-methoxy-4-methyl-5-methylthiothiophene-2-carboxamide, N-[(1-ethyl-2-pyrrolidinyl)methyl]-3-methoxy-4-methyl-5-methylsulphinylthiophene-2-carboxamide, N-[(1-ethyl-2-pyrrolidinyl)methyl]-3-methoxy-4-methyl-5-methylsulphonylthiophene-2-carboxamide, N,N-dimethylaminoethyl-3-methoxy-4-methyl-5-methylthiothiophene-2-carboxamide, N,N-diethylaminoethyl-3-methoxy-4-methyl-5-methylthiothiophene-2-carboxamide, and their pharmaceutically-acceptable salts.

The novel compounds of the invention are useful both as the free compound and as salts, for example the pharmaceutically-acceptable acid addition salts such as salts derived from non-toxic inorganic acids, for eample, hydrochloric acid, nitric acid, phosphoric acid, sulphuric acid, hydrobromic acid, hydriodic acid and phosphorous acid, as well as salts derived from nontoxic organic acids such as aliphatic mono- and dicarboxylic acids, especially fumaric acid, phenyl-substituted alkanoic acids, hydroxyalkanoic and hydroxyalkanioic acids, aromatic acids, aliphatic and aromatic sulphonic acids. In additional to pharmaceutically-acceptable salts, other salts are included such as, for example, those with picric or oxalic acids; they may serve as intermediates in the purification of the compounds or in the preparation of other, for example pharmaceutically-acceptable acid addition salts, or are useful for identification, characterisation or purification of the bases.

It will be appreciated that the compounds of the invention can contain one or more assymetric carbon atom which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form. Such pure forms can be separated from the racemic mixture, or, alternatively, the enantiomers can be prepared by utilising optically active amines in the preparation of the compounds. The preferred enantiomer is the laevorotatory (−) form.

The invention also includes a process for producing a compound according to formula (I) above, which comprises reacting a compound of the formula

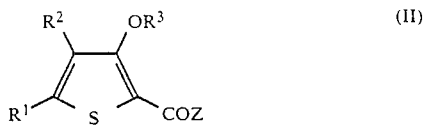

in which $R^1$, $R^2$ and $R^3$ have the values assigned them above, and Z is halo, —OH or —OR where R is a leaving group such as $C_{1-4}$ alkyl, with an amine of the formula X $NH_2$ in which X has the above-assigned values.

The reaction is preferably carried out at a temperature of from 0° C. to 200° C., more preferably from 0° C. to 100° C., in an inert organic solvent such as, for example a haloalkane, such as, dichloromethane. When Z is —OH a coupling agent is preferably employed such as a coupling agent commonly used in peptide synthesis, for example carbonyldiimidazole. When Z is OR, it is often desirable to carry out the reaction at a higher temperature, for example from 100° C. to 200° C. The preferred reactions are those in which the reactant is one of formula (II) in which Z is halo or —OH.

Compounds of formula (II) are either readily available or can be prepared from known compounds by conventional synthesis. For example, the compound of formula (II) can be prepared by alkylation of an intermediate of the formula

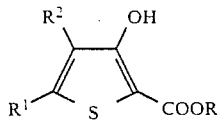

where R is hydrogen or $C_{1-4}$ alkyl. Such compounds can, in their turn, be prepared by condensation of the appropriate aldehydo- and mercapto-esters

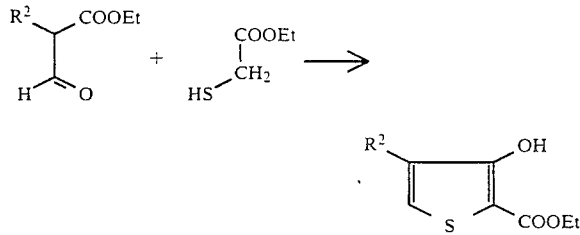

followed by alkylation of the hydroxyl group and reaction with sulphuryl chloride and appropriate mercaptan or alkylsulphonate reactant.

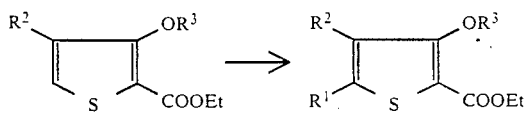

The appropriate sulphinyl intermediate can be prepared by oxidation of the compound in which $R^1$ is alkylthio by use of an oxidising agent such as for example m-chloroperbenzoic acid.

The amine reactants of formula (III) are known compounds or are made by methods known in the art. For example, such cycloamine compounds are disclosed in J. Chem. Soc. (1957) 3165, South African Patent 69 00983, French Patent 2 534 255, and in Chemical Abstracts 66 2432 g (1967), and the 2-amino-8-azanortropane starting reactants are disclosed in French Patent 2 499 570.

As mentioned above, the compounds of the invention in free base and pharmaceutically-acceptable acid addition salt form have useful central nervous system activity. They are also of low toxicity. Their activity has been demonstrated by testing in animal models using well-established procedures. More specifically, the compounds have been shown to block apomorphine induced climbing in mice according to the method of Costall, Naylor and Nohria (European J. Pharmacol. 50, 39; 1978), and/or to block a conditioned avoidance response in rats according to the method of Jacobsen and Sonne (Acta Pharmacol. et Toxacol. 11, 35, 1955), at doses below 50 mg/kg when administered intraperitoneally.

These tests show that the compounds of the invention block post-synaptic dopamine receptors and are accordingly indicated for the treatment of emesis, depression, anxiety and psychotic conditions such as schizophrenia and acute mania.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutically-acceptable salts of the invention will normally be administered orally or by injection and, for this purpose, the compounds and salts will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptable diluent or carrier therefor. Such compositions form part of the present invention. In making such compositions of the present invention, the active ingredient will usually be mixed with a carrier or diluent. Additionally or alternatively it may be enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phosphate, alginates, tragacanth, gelatin, syrup, methyl cellulose, methyl and propylhydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use or injectable solutions for parenteral use. Preferably the compositions are formulated in a dosage unit form, each dosage containing from 1 to 200 mg more usually 5 to 100 mg, of the active ingredient.

The invention is illustrated by the following Examples.

EXAMPLE 1

(a) Methyl 3,3-dimethoxy-2-methyl propionate

A solution of 96 ml of bromine (1.8 mol) in 100 ml of carbon tetrachloride was added to 180 g of methyl α-methylacrylate while stirring, keeping the temperature around −10° C.

Once the addition had been completed, the solvent was evaporated and residue distilled. Methyl, 2,3-dibromo-2-methyl propionate, (b.p.: 80°–83° C., 11 mmHg) was obtained.

The dibromo derivative was dissolved in 332 ml of methanol and was added dropwise to a solution of 55 g of sodium in 624 ml of methanol. The mixture was heated to reflux and then stirred over night at room temperature. The solvent was evaporated to half volume, and the precipitated sodium bromide filtered.

The filtrate was concentrated under reduced pressure and the residue partitioned between water and ethyl ether. The organic layer was separated, dried over sodium sulphate and the solvent evaporated to leave an oil which was distilled to give 220 g of methyl 3,3-dimethoxy-2-methyl propionate, (b.p. 66°–67° C., 10 mmHg).

(b) Methyl 3,3-bis(methoxycarbonyl methylthio)-2-methyl-propionate

To a mixture of the acetal of (a) above (0.1 mol) and methylthioglycolate (0.2 mol), 1 ml of boron trifluoride etherate was added, the mixture was heated, and methanol distilled off. The reaction was cooled and the residue used without further purification in the next step.

(c) Methyl 3-hydroxy-4-methylthiophene-2-carboxylate

Dithioacetal of (b) above (0.08 mol) was dissolved in 120 ml of 2N sodium methoxide in methanol and stirred over night at room temperature.

The solvent was evaporated and the residue treated with 50 ml of water. The precipitate was acidified with 2N hydrochloric acid and extracted with ether. The organic layer was dried over sodium sulphate and the solvent evaporated, b.p. 60°–62° C. (0.05 mmHg).

(d) Methyl 2-chloro-4-methyl-3-oxo-2,3-dihydrothiophene-2-carboxylate

N-Chlorosuccinimide (0.027 mol) was added to a stirred solution of the hydroxythiophen of (c) above (3 g) in 8 ml of carbon tetrachloride.

The mixture was heated at reflux temperature over night. After cooling, the precipitate was filtrated and the solvent evaporated. The residue was recrystallised from hexane, m.p. 52°–54° C.

(e) Methyl 3-hydroxy-4-methyl-5-methoxythiophene-2-carboxylate

The product of (d) above (3 g) was dissolved in 15 ml of methanol and stirred 8 hours at room temperature. The precipitate was filtered and recrystallised from methanol, m.p. 63°–65° C.

(f) Methyl 5-acetylthio-3-hydroxy-4-methylthiophene-2-carboxylate

The chlorothiophene of (e) above (0.016 mol) in 10 ml of acetic acid was added to a solution of 0.9 ml of concentrated sulphuric acid in 10 ml of acetic acid. Whilst stirring, thioacetic acid (0.016 mol) was added and the mixture stood at room temperature for eight hours. Filtration of the precipitate afforded 75% of acetylthiothiophene which was recrystallised from hexane, m.p. 112°–114° C.

(g) Methyl 3-hydroxy-5-mercapto-4-methylthiphene-2-carboxylate

The acetylthiothiophene of (f) above (10 mmol) was added to 30 ml of 1M potassium hydroxide in methanol. After acidification of the mixture, the mercapto thiophene was obtained, recrystallising from hexane, m.p. 86°–88° C.

(h) Methyl 3-methoxy-4-methyl-5-methylthiothiophene-2-carboxylate

The mercaptothiophene of (g) above (10 mMol) was dissolved in 25 ml of anhydrous acetone and potassium carbonate (20 mmol) added. The mixture was stirred for ten minutes and dimethylsulphate (20 mmol) added. The mixture was heated under reflux for 5 hours, the solvent removed and the residue partitioned between water and ethyl acetate. The organic phase was isolated, washed with water and dried over sodium sulphate.

After evaporation of the solvent an oil was obtained, which was used without further purification.

(i) 3-Methoxy-4-methyl-5-methylthiothiophene-2-carboxylic acid

The methoxycarbonylthiophene of (h) above (15 mmol) was stirred in a solution of sodium hydroxide (1.2 g) in 45 ml of water. The mixture was heated under reflux for 1 hour. After cooling, the solution was acidified with dilute hydrochloric acid, and extracted with ethyl acetate. The organic phase was washed with brine and dried over sodium sulphate. Evaporation of the solvent yielded the carboxylic acid which was recrystallised from ethyl acetate, m.p. 126°–128° C.

(j) (−)N-{(1-ethyl-2-pyrrolidinyl)methyl}-3-methoxy-4-methyl-5-methylthiothiophene-2-carboxamide, fumarate To a solution of 3-methoxy-4-methyl-5-methylthio-thiophene-2-carboxylic acid (1.93 g) in dry dichloromethane (50 ml) under nitrogen, 1,1-carbonyl-diimidazole was added. After stirring for 1 hour at room temperature (−)-2-aminomethyl-1-ethylpyrrolidine was added and the solution stirred over night.

The reaction mixture was extracted with 3×10 ml of 3N hydrochloric acid. The organic layer was washed with aqueous sodium bicarbonate, then with water. After drying over sodium sulphate and evaporating the solvent, an oil was obtained which was dissolved in hot ethyl acetate and fumaric acid (0.90 g) added. After heating to reflux, the fumarate salt precipitated and was filtered from the cooled solution, m.p. 95°–96° C.

EXAMPLE 2

N-(2-Diethylaminoethyl)-3-methoxy-4-methyl-5-methylthiothiophene-2-carboxamide, fumarate To a solution of 1,1-carbonyldi-imidazole (800 mg) in 25 ml tetrahydrofuran under a nitrogen atmosphere was added 3-methoxy-4-methyl-5-methylthiothiophene-2-carboxylic acid 1.1 g). After stirring for 1 hour freshly distilled N,N-diethylethylenediamine (0.75 ml) was added and stirring was continued for 20 hours. The mixture was partitioned between 5M hydrochloric acid and ethyl acetate. The aqueous was made alkaline with 30% ammonia solution and extracted with dichloromethane. The extract was washed with water, dried over magnesium sulphate, and the solvent evaporated to leave the crude amine which was converted to the fumarate salt, crystallising from ethyl acetate.

The following Examples illustrate the preparation of typical formulations containing an active ingredient according to the invention.

EXAMPLE 3

Hard gelatin capsule

Each capsule contains
Active ingredient: 10 mg
PEG 4000: 250 mg

The PEG 4000 is melted and mixed with the active ingredient. Whilst still molten the mixture is filled into capsule shells and allowed to cool.

EXAMPLE 4

Tablet

Each tablet contains
Active ingredient: 10 mg
Calcium carbonate: 300 mg
Magnesium stearate: 10 mg
Starch: 30 mg
Hydroxypropylmethylcellulose: 10 mg
Iron oxide: 4 mg The active ingredient is granulated with calcium carbonate and starch. The dried granulate is blended with lubricant and disintegrant and compressed into tablets of the required dosage strength. The tablet may then be coated.

EXAMPLE 5

Injection

Active ingredient: 10 mg
Water: 1 ml

The active ingredient is dissolved in water and distributed into vials, ampoules or pre-pack syringes using appropriate equipment. The product is sterilised.

We claim:

1. A compound of the formula

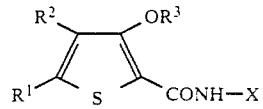

in which $R^1$ is $C_{1-4}$ is alkylthio, $C_{1-4}$ alkylsulphinyl of $C_{1-4}$ alkylsulphonyl, $R^2$ is $C_{1-4}$ alkyl, $R^3$ is $C_{1-4}$ alkyl or $C_{2-4}$ alkenyl, and X is (i) $-(CH_2)_nN(R^4)_2$ where each $R^4$ independently is $C_{1-4}$ alkyl, $C_{2-4}$ alkenyl or optionally substituted $C_6H_5CH_2-$, and n is 1, 2 or 3, or (ii) a 5- to 8-membered alicyclic group containing one or two nitrogen atoms and directly attached to the amido nitrogen or attached by a $C_{1-3}$ alkylene chain; and salts thereof.

2. A compound according to claim 1 in which X is a 5- to 8-membered alicyclic group containing one or two nitrogen atoms and directly attached to the amido nitrogen or attached by a $C_{1-3}$ alkylene chain.

3. A compound of the formula

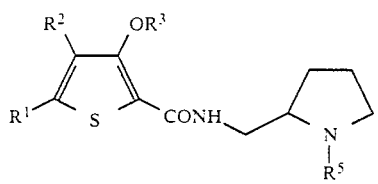

in which $R^1$ is $C_{1-4}$ alkylthio, $C_{1-4}$ alkylsulphinyl or $C_{1-4}$ alkylsulphonyl, $R^2$ is $C_{1-4}$ alkyl, $R^3$ is $C_{1-4}$ alkyl or $C_{2-4}$ alkenyl, and $R^5$ is $C_{1-4}$ alkyl; and salts thereof.

4. A compound according to claim 3, in which $R^1$ is methylthio, methylsulphinyl or methylsulphonyl, and $R^2$ and $R^3$ are methyl.

5. A compound according to claim 4, in which $R^1$ is methylthio.

6. A method of treating an animal, including a human, suffering from or susceptible to a disorder of the central nervous system, which comprises administering an effective amount of a compound according to claim 1, or a pharmaceutically-acceptable salt thereof.

* * * * *